(12) United States Patent
Khosla et al.

(10) Patent No.: US 6,974,664 B2
(45) Date of Patent: Dec. 13, 2005

(54) SCREENING METHOD FOR CANCER THERAPEUTICS AND STABLE ANTITUMOR DRUG

(75) Inventors: Chaitan Khosla, Palo Alto, CA (US); Art Salomon, San Diego, CA (US)

(73) Assignee: The Board of Trustees of the Leland Stanford University, Palo Alto, CA (US)

( * ) Notice: Subject to any disclaimer, the term of this patent is extended or adjusted under 35 U.S.C. 154(b) by 431 days.

(21) Appl. No.: 09/916,233

(22) Filed: Jul. 25, 2001

(65) Prior Publication Data

US 2002/0077300 A1 Jun. 20, 2002

Related U.S. Application Data

(63) Continuation-in-part of application No. 09/854,257, filed on May 11, 2001, now Pat. No. 6,548,485.
(60) Provisional application No. 60/203,731, filed on May 12, 2000, and provisional application No. 60/220,779, filed on Jul. 25, 2000.

(51) Int. Cl.$^7$ .................................................. C12Q 1/00
(52) U.S. Cl. ........................................................... 435/4
(58) Field of Search ............................. 435/21, 31, 32, 435/4; 430/7.31

(56) References Cited

U.S. PATENT DOCUMENTS 6,376,211 B1 * 4/2002 Little et al. .................... 435/21

OTHER PUBLICATIONS

Hayakawa et al., J. Am. Chem. Soc. (1998) 120:3524–3525.
Kim et al., Antibiot. (1997) 50:628–630.

* cited by examiner

*Primary Examiner*—Elli Peselev
(74) *Attorney, Agent, or Firm*—Morrison & Foerster LLP

(57) ABSTRACT

Screening methods and methods of treatment taking advantage of the mode of action of apoptolidin and its analogs are described.

4 Claims, 11 Drawing Sheets

FIG. 2A
Bafilomycin

FIG. 2B
Truncated Apoptolidin

SCREENING METHOD FOR CANCER THERAPEUTICS AND STABLE ANTITUMOR DRUG

CROSS-REFERENCE TO RELATED APPLICATIONS

This is a CIP of U.S. Ser. No. 09/854,257 filed May 11, 2001 now U.S Pat. No. 6,548,485 which claims priority under 35 U.S.C. §119(e) to U.S. provisional application Serial No. 60/203,731 filed May 12, 2000. This application also claims priority under 35 U.S.C. §119(e) to U.S. provisional application Serial No. 60/220,779 filed Jul. 25, 2000. The contents of all the above applications are incorporated herein by reference.

ACKNOWLEDGEMENT OF GOVERNMENT SUPPORT

The work herein is supported by a grant from the National Institutes of Health. The U.S. government has certain rights in this invention.

TECHNICAL FIELD

The invention relates to screening methods for tumor therapeutics and to methods to treat tumors using compounds identified by these methods. More specifically, the invention concerns analogs of apoptolidin which are cytotoxic to tumor cells and to compounds which accentuate the effect of these analogs.

BACKGROUND ART

Two reports originating from a research team headed by H. Seto describe a novel apoptosis-inducing macrolide from Nocardiopsis sp., designated apoptolidin. See, Kim, J., et al., *J. Antibiot.* (1997) 50:628–630; Hayakawa, Y., et al., *J. Am. Chem. Soc.* (1998) 120:3524–3525. These workers demonstrated that cancer cells could be selectively sensitized to apoptosis by this natural product. A truncated form of apoptolidin which lacks two of the natively occurring glycosylation residues is also described. The truncated form was prepared in 12% yield by treating native apoptolidin with acid in methanol. While only 1% of the cytotoxic activity of the apoptolidin itself was demonstrated in an assay involving FACS staining for Annexin V and by an MTT assay, at least with respect to the cell lines MCF-7, and the murine B lymphoma cell line LYas, the truncated form was more stable.

The Seto group demonstrated that apoptolidin induces apoptosis in cells expressing the E1A oncogene, but not in non-tumor cells or in cells expressing the ras or src oncogene.

It has now been found that the cellular target of apoptolidin, as well as that of other antifungals such as oligomycin, is mitochondrial ATP synthase. This enzyme is embedded in the mitochondrial membrane and the catalytic activity resides in a portion of the protein which extends inside the mitochondrion. It is responsible for phosphorylation of ADP in the oxidative phosphorylation reactions associated with aerobic metabolism.

Identification of this enzyme as a target provides a means to screen compounds for antitumor activity and elucidation of the mechanism by which apoptolidin acts to effect apoptosis provides a further rationale for the design of treatments for enhancing the effect of compounds which exert their antitumor effects in a manner analogous to that of apoptolidin.

DISCLOSURE OF THE INVENTION

In one aspect, the invention is directed to a stabilized derivative of apoptolidin which lacks the oleandrose and olivomycose sugars. The derivative is stable under physiological conditions and a potent selective antitumor agent.

Thus, in one aspect, the invention is directed to a compound of the formula and the pharmaceutically acceptable esters thereof.

In other aspects, the invention is directed to pharmaceutical or veterinary compositions of the compounds of formula 1 and to methods to treat tumors by administering the compound of formula 1 or a pharmaceutical composition thereof. In still other aspects, the invention is directed to a method to synthesize the compound of formula 1 by conversion from apoptolidin and optional esterification.

The invention is also directed to a method to identify compounds with antitumor activity which method comprises assessing the ability of candidate compounds to inhibit the mitochondrial ATP synthase. Although the biological function of this enzyme is to effect oxidative phosphorylation of ADP, the enzyme may be assayed in a much more simple protocol in vitro by assessing its ATPase activity—i.e., the reverse reaction. Standard assays for the ATPase activity of this enzyme are well known.

Thus, in one aspect, the invention is directed to a method to identify a compound which will effect apoptosis selectively in tumors which method comprises assaying said compound most conveniently for its ability to inhibit the ATPase activity of mitochondrial ATP synthase whereby a compound which is able to effect such inhibition is identified as an antitumor agent.

Suitable candidate compounds comprise a broad range of organic molecules; however, compounds with a particularly high probability for success in the assay are structural analogs of apoptolidin. Because the nucleotide sequences encoding the synthases which catalyze the production of apoptolidin are available, and because suitable modification techniques, such as those described in U.S. Pat. No. 5,962,290 and U.S. Ser. No. 09/073,538 filed May 6, 1998, both incorporated herein by reference, are available, it is possible readily to synthesize a wide range of analogs. By systematic modification of the apoptolidin synthase enzymes, the nature of the starter and extender units for the construction of this molecule can be altered. In addition, the number of and nature of the glycosylation residues can also be modified, as well as can other tailoring aspects be altered.

Further, because as described herein, cells which rely on anaerobic degradative pathways for the formation of ATP are not dependent on this synthase for ATP production, cells which are inhibited from utilizing the alternative fermentation pathway have enhanced susceptibility to treatment with inhibitors of ATP synthase. Therefore, assessment of the ability of a compound to suppress the alternative fermentative pathway permits an assessment of its ability to enhance the apoptotic activity of apoptolidin. Thus, in another aspect, the invention resides in a method to identify a compound which will enhance apoptolidin-like activity in tumors which method comprises assessing the ability of the compound to suppress anaerobic pathways in cellular metabolism, whereby a compound that inhibits said pathways is identified as a compound which will enhance apoptolidin-like activity.

Of course, inhibitors of the alternative anaerobic metabolic pathway are known. Thus, in an additional aspect, the invention is directed to a method to kill tumor cells which method comprises contacting said cells with an inhibitor of mitochondrial ATP synthase, optionally in the presence of at least one compound that inhibits the fermentative anaerobic pathway in tumor cells. In still another aspect, the invention is directed to a method to sensitize tumor cells or other cells to apoptosis by suppressing the anaerobic metabolic pathway for glucose.

MODES OF CARRYING OUT THE INVENTION

In one aspect the invention is directed to the compound of formula 1 and its lower alkyl or substituted alkyl esters. The compound of formula 1 per se is preferred. The alkyl esters are formed in a conventional manner from the compound of formula 1 by treatment with suitable acyl derivatives. The acyl moiety may contain 1–6 carbons, and may optionally be substituted by hydroxy or methoxy. Five hydroxyl groups are available for esterification; the invention includes compounds in which one or more of these groups are esterified.

The invention compounds also include the ethers formed from the five available hydroxyl groups; ethers may be formed from the relevant alkyl halides, which halide contain 1–2C. As with respect to the ester derivatives, one, two, or more of the hydroxyls may be in the form of ethers. Mixed esters and ethers are also included within the scope of the invention. Synthesis of these derivatives is conventional.

The compound of formula 1 also contains chiral centers; the compounds of the invention include stereoisomers of the compound of formula 1 and mixtures of stereoisomers thereof.

The compound of formula 1 can readily be prepared by treating apoptolidin in an alcoholic acid solution at ambient temperatures for several hours. The conditions of time and temperature may vary and optimal conditions for preparation of the compound of formula 1 from apoptolidin can be readily obtained by straightforward optimization techniques.

Figure 1A:
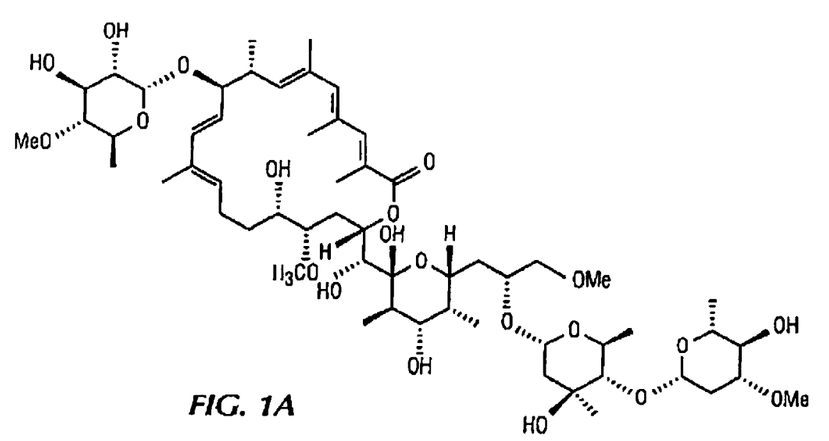
FIG. 1 shows a scheme for the conversion of apoptolidin to the invention compound.
Figure 1B:
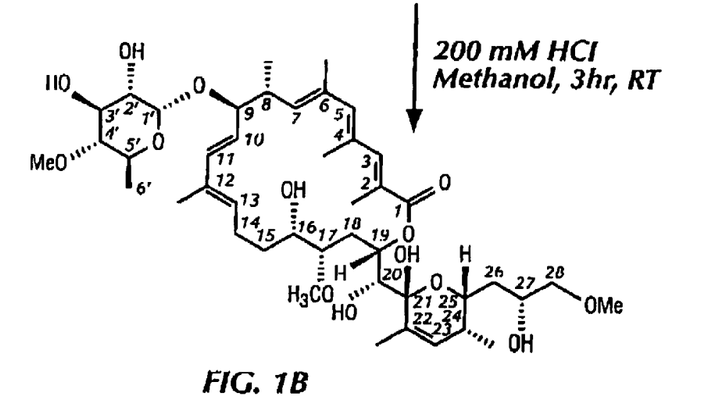
Figure 2A:
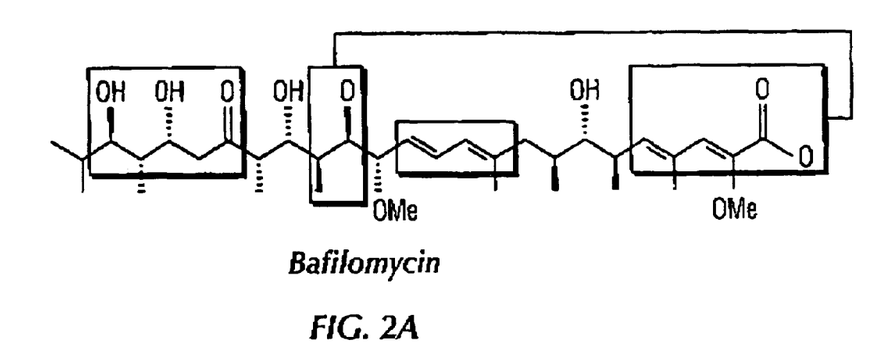
FIG. 2 shows a comparison of the invention compound with bafilomycin.
Figure 2B:
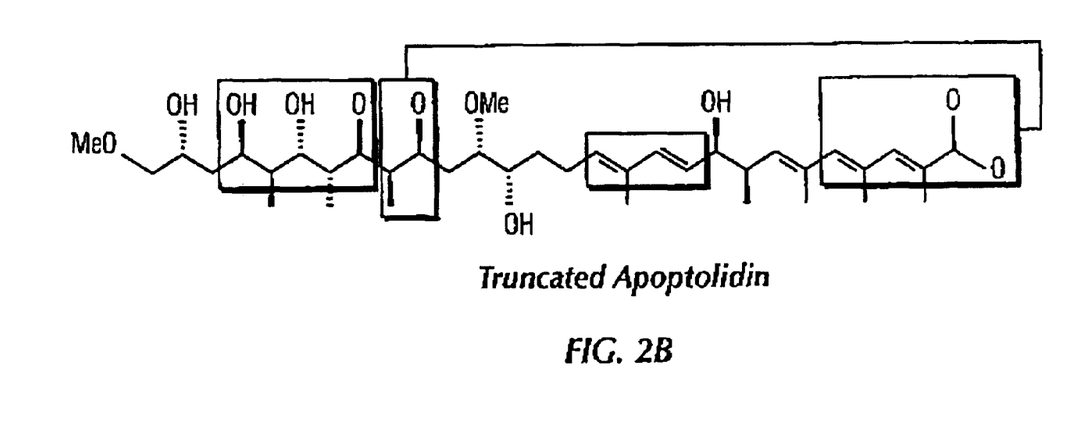

Applicants believe that the compound of formula 1 enhances apoptosis susceptibility by cancer cells by targeting vacuolar H±-ATPases (V-ATPases). FIG. 2 shows the structural similarity between the parent compound apoptolidin and bafilomycin which is a known inhibitor of V-ATPases. Others have shown that the dienic system of the macrolide ring of bafilomycin is crucial to its activity while modifications to the hemiketal ring do not seem to be crucial. (Gagliardi, S., et al., *J. Med. Chem.* (1998) 41:1883–1893.) The compound of formula 1, similarly, contains a dienic macrolide ring.

Figure 3:
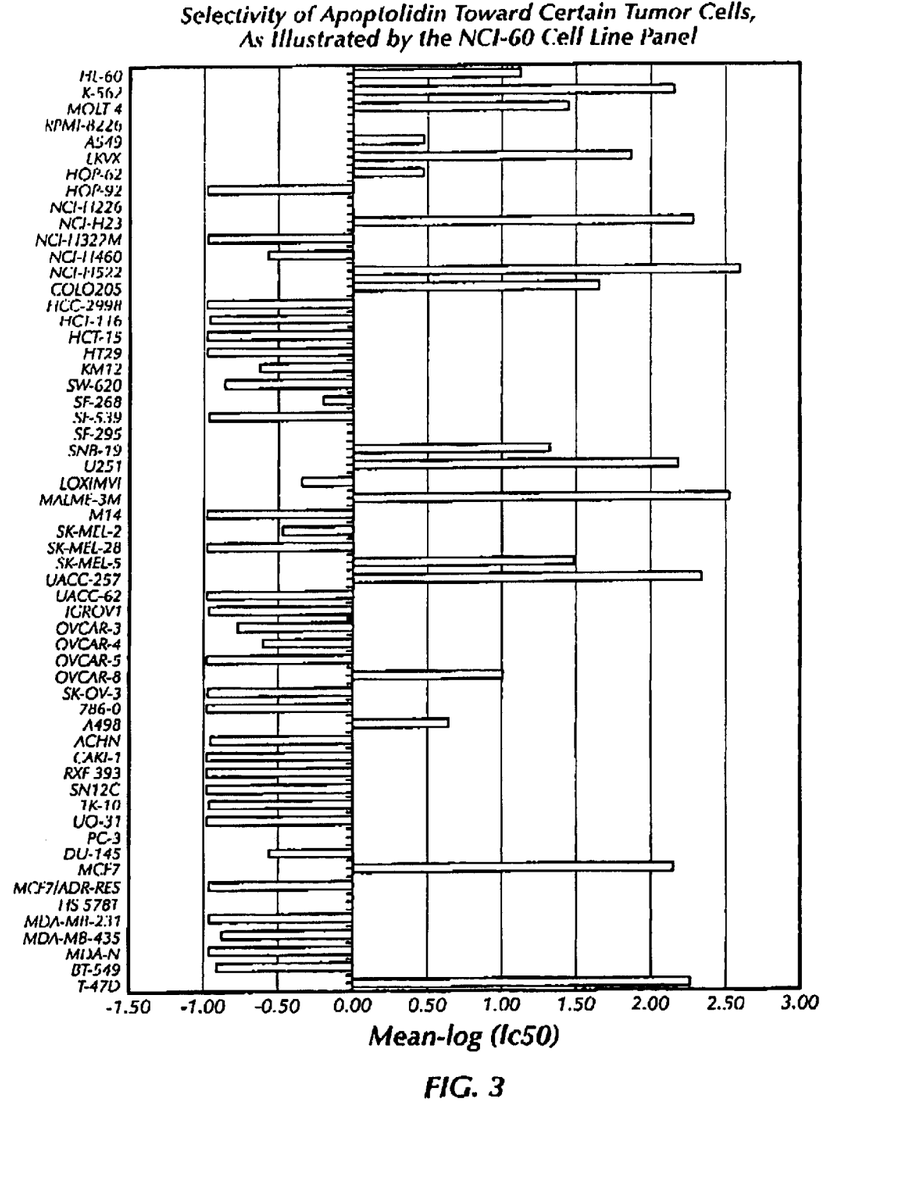
FIG. 3 shows a graph of the ability of apoptolidin to effect apoptosis in various human tumor cell lines.

Apoptolidin itself has been assayed for its ability to exert a cytotoxic effect on a variety of human cell lines maintained by the NCI- i.e., the NCI-60 cell line panel. Cytotoxicity is measured by treating with Annexin V which preferentially binds to phosphatidyl serine exposed on the surface of apoptotic and necrotic cells and propidium iodide which stains cells with permeabilized cytosolic membranes. Briefly, the cells are stained with 5 µl/test Annexin V—FITC (Becton Dickinson, Franklin Lakes, N.J.) for 15 minutes and washed 3 times, then stained with 1 µg/ml propidium iodide and washed 2 times. The cells are then analyzed on the Facscan (Becton Dickinson) and the percentage of Annexin V and propidium iodide positive cells is quantified. The results on this panel are shown in FIG. 3, where the median value of $IC_{50}$ is arbitrarily set as 0 and the $IC_{50}$ values of apoptolidin against various cell lines in the panel graphed according to their logarithmic difference from the median. The total spread of $IC_{50}$ values is greater than 3 logs, probably an underestimate since apoptolidin reaches its solubility limit at 1 log below the median $IC_{50}$.

An analysis of the data in FIG. 3 led to the conclusion that cells which exhibit low requirements for ATP are relatively resistant to apoptolidin. Among those cells which have high ATP requirements, aerobic cells are sensitive, while anaerobic cells are resistant. This conclusion is consistent with the further findings that killing induced by apoptolidin was independent of p53 status, was inhibited by Bcl-2, and was dependent on the action of caspases including caspase-9; in addition, PARP was completely cleaved in the presence of 1 µM apoptolidin within 6 hours (data not shown). These results suggested that apoptolidin target a mitochondrial protein.

Further insight was gained by structural comparisons between apoptolidin and other macrolides. The structural similarity between the apoptolidin aglycone and oligomycin, which is a known inhibitor of mitochondrial FOF1-ATP synthase was of particular significance.

Figure 4:
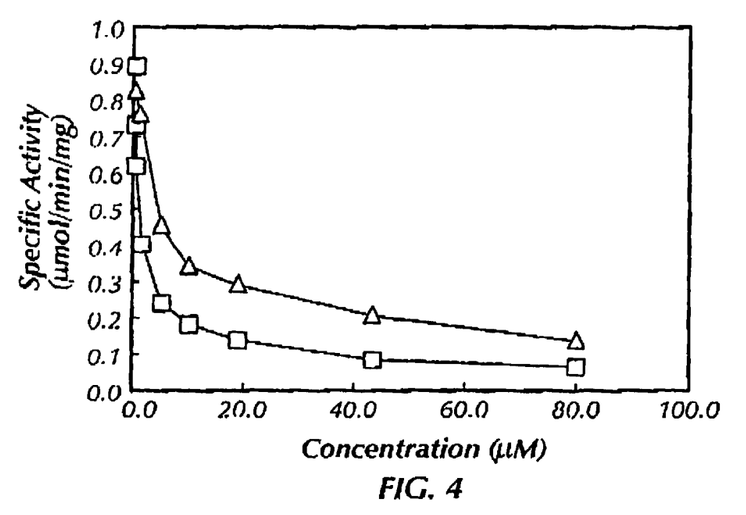
FIG. 4 shows the ability of apoptolidin to inhibit yeast mitochondrial FOF1-ATP synthase as a function of concentration.

As is demonstrated by the applicants herein, apoptolidin inhibits the activity of yeast mitochondrial FOF1-ATP synthase, isolated as described in Preparation A. As explained above, the ability to inhibit mitochondrial ATP synthase can be measured conveniently in vitro by measuring the effect of the compound on the ATPase activity of this enzyme. As shown in FIG. 4, apoptolidin and oligomycin both inhibit the specific ATPase activity of this enzyme measured as μmole/min/mg protein of NAD+ produced. The assay is that described in Example 4 hereinbelow where the combination of pyruvate kinase and LDH effect conversion of phosphoenol pyruvate to lactate in the presence of ATP and NADH. With increasing concentrations of either drug, the specific activity of the enzyme rapidly declines. The calculated $K_i$ values for oligomycin and apoptolidin are 1 μM and 5 μM respectively. Although the observed $K_i$ for apoptolidin is five-fold higher than that for oligomycin, this may be an underestimate of the potency of apoptolidin. Apoptolidin exhibits a strong pH dependence in its stability; although the natural product is stable under acidic conditions, it rapidly degrades under alkaline conditions. Mitochondrial ATPase activity assays are typically performed at pH 8. Thus, the true $K_i$ for apoptolidin may be lower than that observed herein and accounts for the observation the $IC_{50}$ values for apoptolidin against both LYas as well as MCF7 cells are substantially lower than the measured $K_i$ against mitochondrial ATPase. This difference might be explained by a preference for mammalian ATPase over yeast ATPase, or by the possibility that apoptosis via this pathway is a dominant phenotype.

The assay described above or similar assays for ATPase activity can thus be used to screen candidates for their ability to effect apoptosis selectively in tumor cells. As mentioned above, although any compound could be a candidate, most suitable compounds are those which are analogous to apoptolidin or oligomycin. Preparation of such analogs is enhanced by the availability of the genes responsible for the synthesis of apoptolidin, so that these genes can be manipulated to modify their requirements for starter and extender units, determination of chain length, and various tailoring reactions. Applicants herein have cloned and characterized an approximately 80 kb segment of chromosomal DNA that comprises the gene cluster that encodes enzymes that produce apoptolidin from the organism described by the Seto group. The genomic clones are 5D6, 3C1 (and its corresponding clone 1F10), and 9A8 (and corresponding clones 11H9 and 12D11). Clone 9A8 comprises sugar biosynthetic and P450 genes and a portion of the polyketide synthase (PKS) genes, and clones 5D6 and 3C1 comprise PKS genes.

Figure 5:
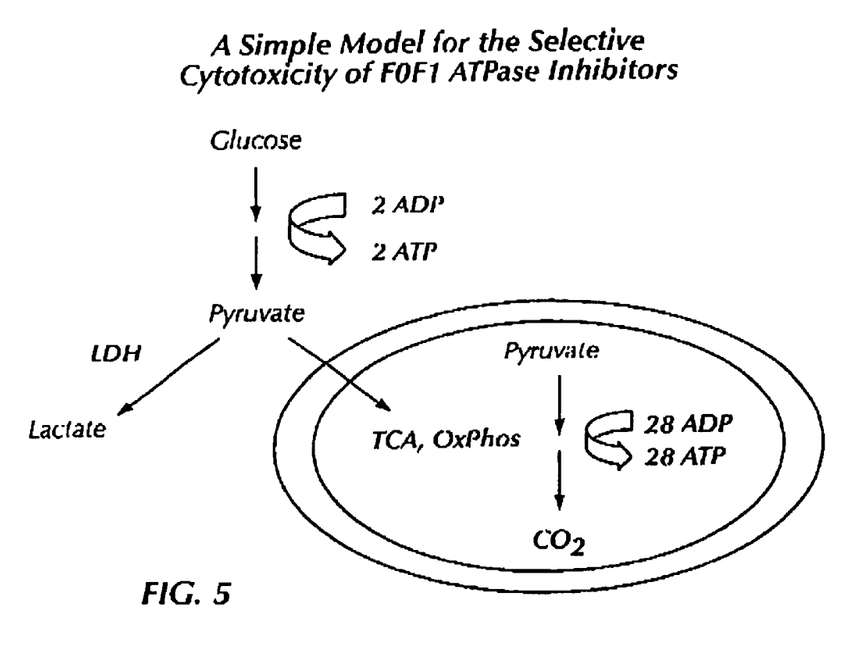
FIG. 5 shows a simplified diagram of the competition between anaerobic and oxidative glucose degradation metabolic pathways.

The relevance of this inhibitory activity with respect to the selectivity according to cell type shown in FIG. 3 can be explained on the basis of the rather simple diagram shown in FIG. 5. In general, there are two sources of ATP available from glucose metabolism. Two ATP's are formed per mole of glucose in the fermentative pathway from glucose to pyruvate to lactate. This ATP formation does not require a specific ATP synthase. The fermentation pathway shown on the left wherein lactate dehydrogenase (LDH) converts pyruvate to lactate is exhibited under anaerobic conditions. No further ATP is formed. However, in the oxidative pathway shown on the right, an additional 28 moles of ATP are created per mole of pyruvate consumed. Aerobic cells with high ATP requirements are sensitive to apoptolidin because they are dependent on this enhanced source of ATP, where the ATP formation is catalyzed by mitochondrial ATP synthase. Anaerobic cells, however, are resistant to apoptolidin because the removal of pyruvate by LDH enhances the formation of the ATP molecules involved in the glucose to pyruvate conversion. Thus, anaerobic cells are able to obtain adequate ATP from a pathway independent of the mitochondrial ATP synthase that is inhibited by apoptolidin.

The anaerobic pathway is particularly important in solid tumors. In early stages of tumor growth, it is typical that inadequate vasculature has been developed to deliver oxygen to the growing mass of tissue and the cells adapt themselves to anaerobic conditions. As the tumor grows, however, it becomes vascularized and the cells are more able to metabolize glucose aerobically. For treatment of tumors which are vascularized and where most of the cells exhibit aerobic metabolism, treatment with apoptolidin or other ATP synthase inhibitors may suffice; however, for treatment of tumors which rely on the anaerobic degradation of glucose, it is preferable to accompany the primary treatment by administering an agent which suppresses the anaerobic pathway, such as deoxyglucose or oxamate.

Figure 6A:
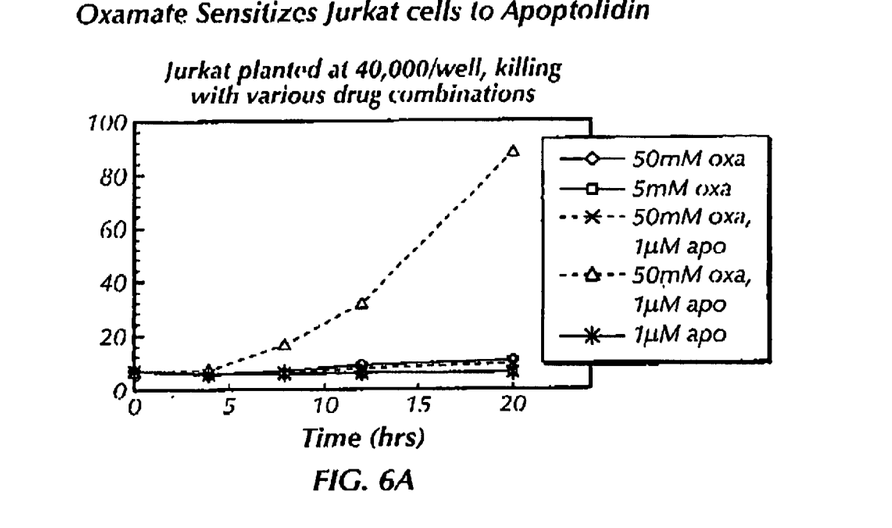
FIG. 6 shows the ability of oxamate to sensitize Jurkat cells to apoptolidin.
Figure 6B:
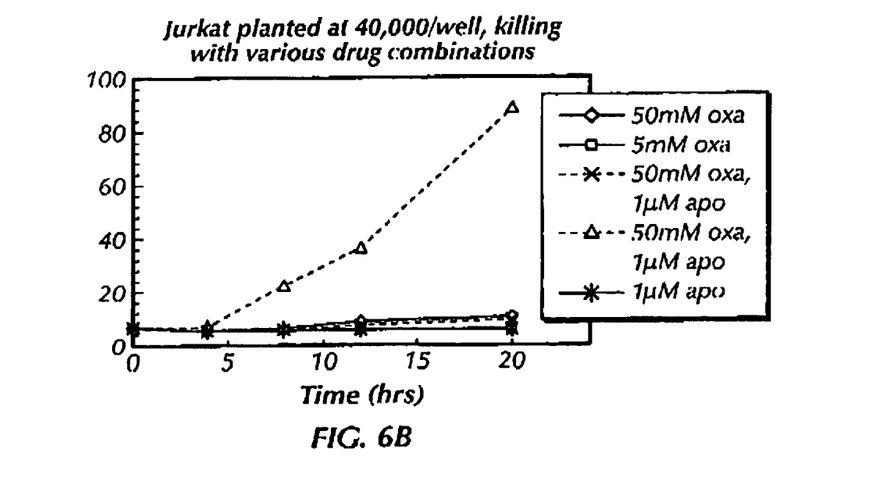

Applicants herein have demonstrated the ability of compounds which are known to repress the anaerobic pathway to sensitize tumor cells to apoptolidin. For example, Jurkat cells planted at 40,000 cells per well and treated with 1 μM of apoptolidin show no cell death over a time period of 20 hours. Supplementing the cultures with 5 mM oxamate does not dramatically change this result; however, when the cells are supplemented with 50 mM oxamate during the treatment with 1 μM apoptolidin, cell death begins to occur after only four hours and by 20 hours, 95% of the cells have been killed. Treatment with these amounts of oxamate alone has no effect. These results are replicated in two experiments as shown in FIG. 6. (Oxamate is a known inhibitor of lactate dehydrogenase; which converts pyruvate to lactate.)

Figure 7A:
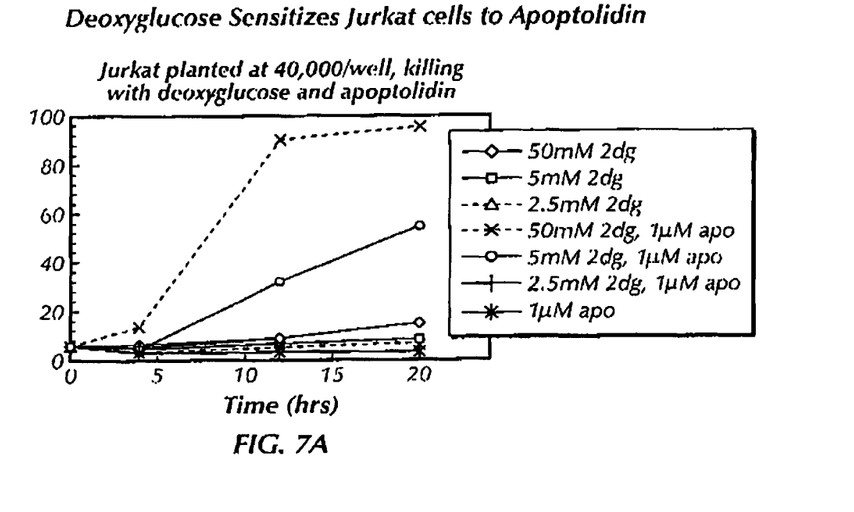
FIG. 7 shows the ability of deoxyglucose to sensitize Jurkat cells to apoptolidin.
Figure 7B:
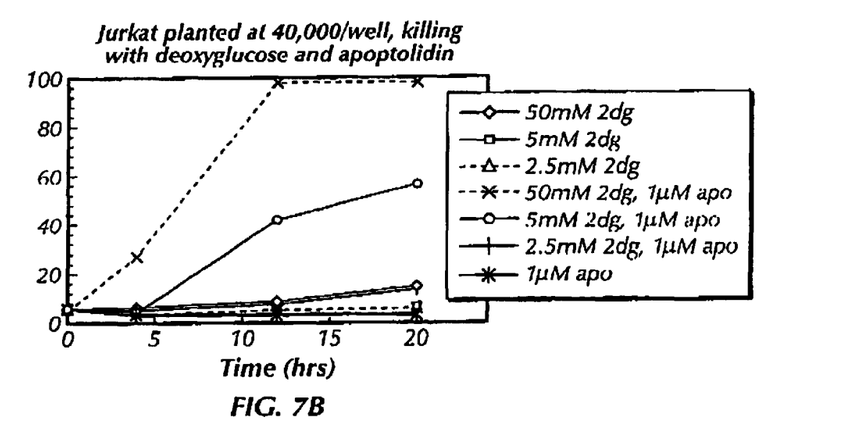

Another compound known to repress the flow of glucose through the fermentative pathway is deoxyglucose which competes with glucose for this pathway but results in a dead end. Similarly replicated experiments wherein Jurkat cells are treated with 1 μM apoptolidin alone and with this concentration of apoptolidin along with various concentrations of deoxyglucose shows that at concentrations of deoxyglucose as low as 5 mM, the ability of apoptolidin to effect apoptosis in this cell line is exhibited. Deoxyglucose alone at the control concentrations has no effect. See FIG. 7.

Figure 8:
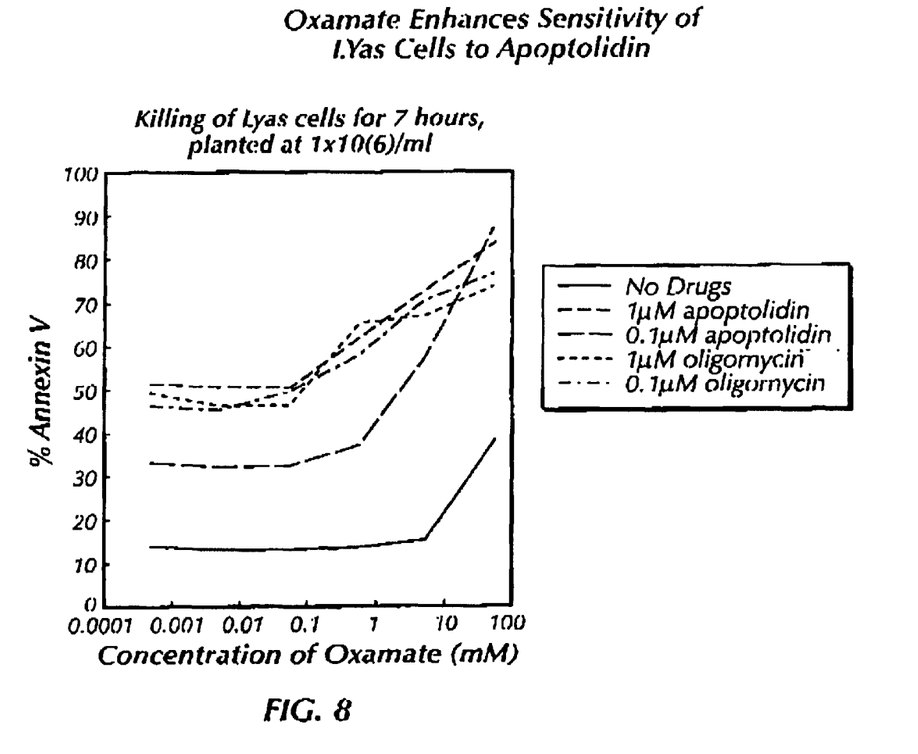
FIG. 8 shows the ability of oxamate to enhance sensitivity of LYas cells to apoptolidin.

Similar results are shown in FIG. 8 for LYas cells, where cells planted at $1 \times 10^6$ ml were assessed for % killing after 7 hours when treated with various concentrations of apoptolidin or oligomycin in the presence of various concentrations of oxamate. When no apoptosis drugs are administered, there is no effect of oxamate up to a concentration of 15 mM. However, at concentrations where the oxamate alone has no effect, both oligomycin and apoptolidin were able to show substantial killing at concentrations as low as 0.1 mM.

Figure 9:
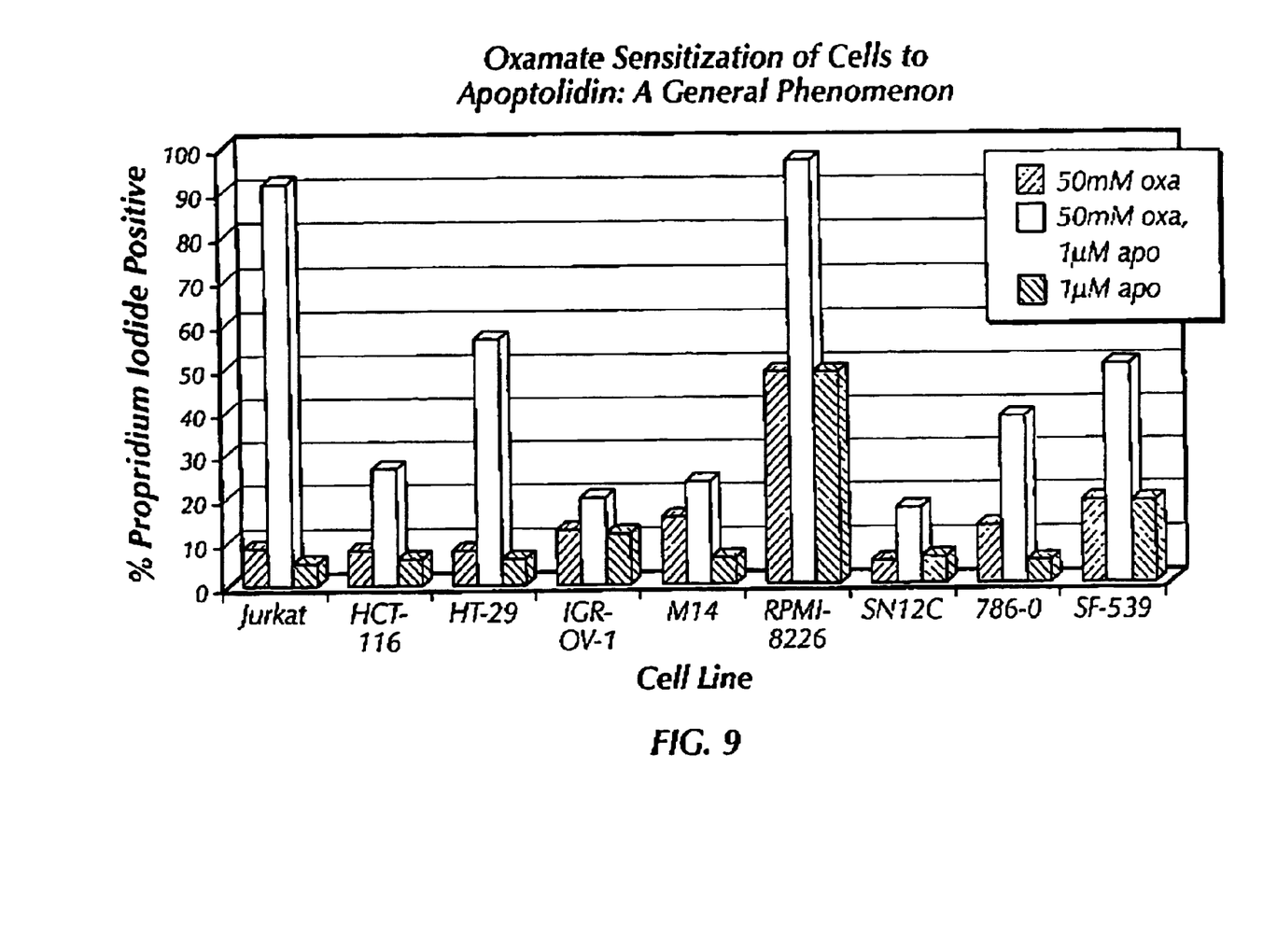
FIG. 9 shows the ability of oxamate to sensitize a variety of cell lines to apoptolidin.
Figure 10:
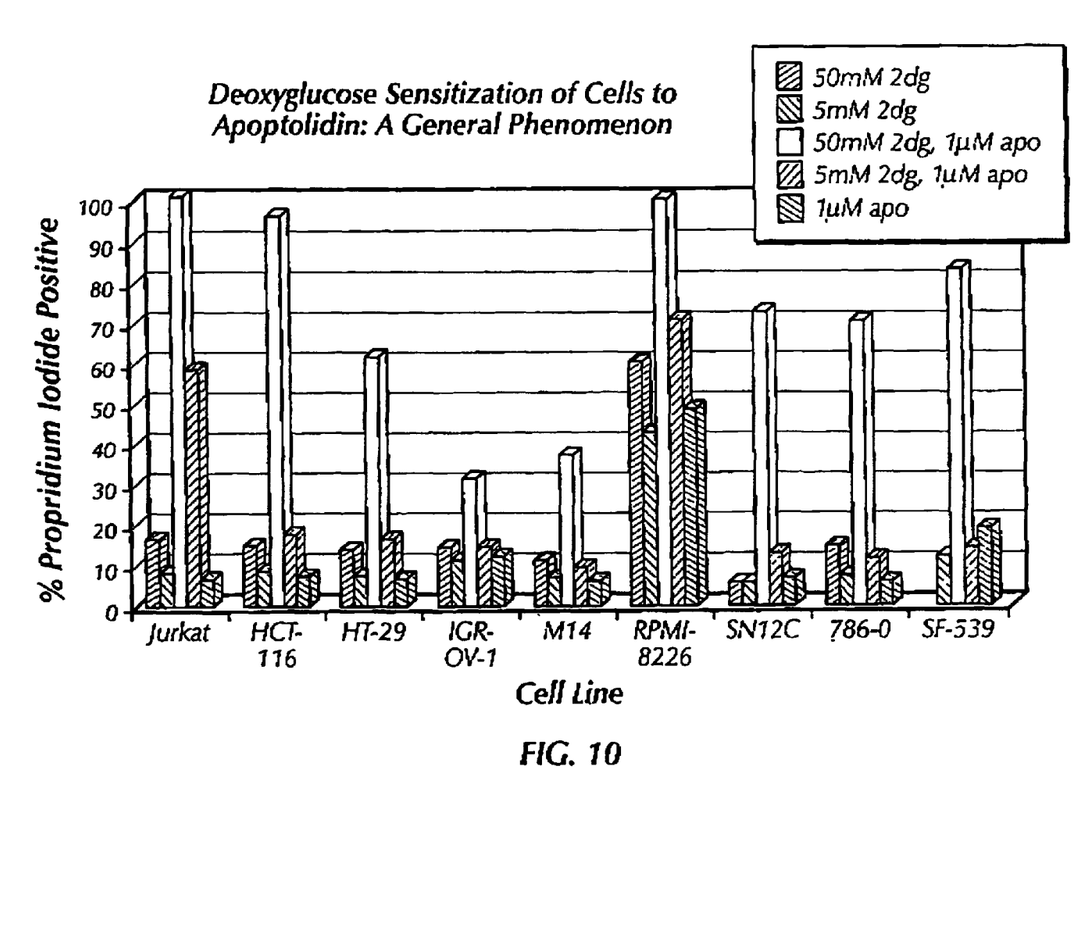
FIG. 10 shows the ability of deoxyglucose to sensitize a variety of cell lines to apoptolidin.
Figure 11:
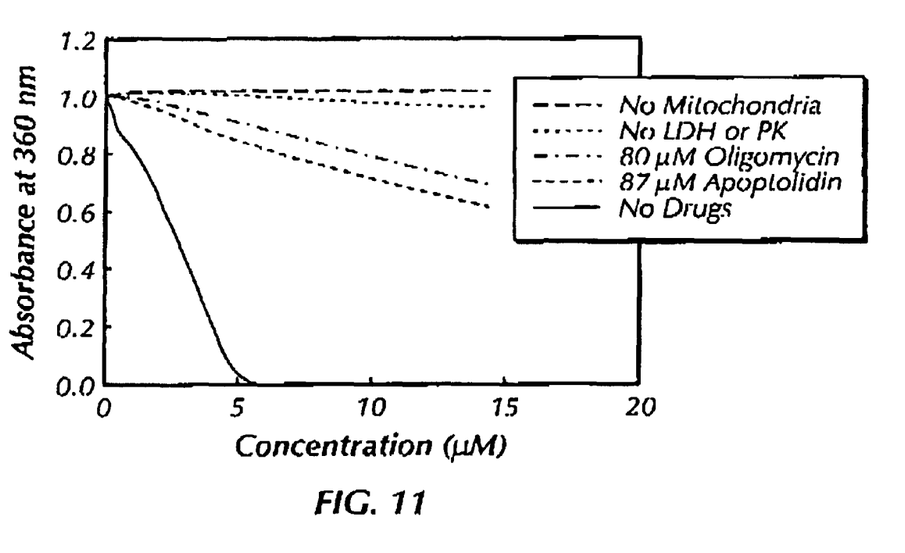
FIG. 11 shows the inhibition of yeast mitochondrial ATPase activity by apoptolidin and oligomycin.

FIGS. 9 and 10 show the generality of this effect with respect to a number of cell lines. The y-axis shows the percentage of cells killed. While apoptolidin is more effective with respect to some cell lines than others, in all cases, the greatest effect is shown when both oxamate and apoptolidin are supplied. The same is true with respect to the results using two deoxyglucose as the enhancer as shown in the FIG. 10.

Thus, it appears that the primary effect of apoptolidin, oligomycin, and related compounds in effecting tumor apoptosis results from their ability to inhibit mitochondrial APT synthase. The discovery of this mechanism permits a design of screening assays for related compounds (or other candidate compounds) for their ability to effect cancer cell killing. The ability of candidate compounds to inhibit the ATPase activity of this enzyme can be readily used as a simple assay for the ability of the compounds to effect apoptosis. This effect can be enhanced by supplying inhibitors of carbon consumption or of lactate formation.

Various agents which are inhibitors of mitochondrial ATP synthase activity thus are identified by the methods of the invention. Apoptolidin, the compound of formula (1), oligomycin, or compounds identified by this screening method are formulated alone or in combination for the treatment of tumor cells in vitro or in vivo. For treatment in vivo, in human or animal subjects, standard formulations such as those set forth in *Remington's Pharmaceutical Sciences*, latest edition, Mack Publishing Co., Easton, Pa., incorporated herein by reference, are used. Thus, the compositions may be suitable for oral administration, including tablets, capsules, syrups, and the like; for injection in physiologically compatible solutions; for mucosal administration wherein the composition contains surfactants; or for transdermal administration which typically includes penetrants. The compositions may contain liposomes or other carriers that facilitate the activity of the active ingredient. Sustained release compositions are also available. Typically, such compounds would be administered by injection; however, a wide variety of other methods is well known, including administration by oral routes, by suppository, or by transmucosal or transdermal administration. Various excipients are known in the art. Suitable dosage ranges are those which result in concentrations of the order of 0.1–100 $\mu$M concentrations in the bloodstream; however, adjustments of these ranges will be made by virtue of the nature of the subject, the nature of the condition, and the judgment of the attending practitioner. In addition, the effective dosage range will depend on the presence or absence of an accompanying administration of an agent which suppresses the anaerobic metabolism of glucose.

By an agent that "suppresses the anaerobic metabolism of glucose" is meant an agent which inhibits the pathway from glucose to lactate in the cell. The inhibition may occur before or after the conversion of pyruvate to lactate. Thus, 2-deoxyglucose inhibits the pathway at the outset; oxamate is an inhibitor of lactate dehydrogenase which effects the conversion to lactate.

While additional compounds which are effective to suppress the anaerobic degradation of glucose can be identified by straightforward screening for this ability, a number of such agents are well known in the art. One or more of these agents, also formulated according to known methods may be administered with the primary treatment in order to enhance the apoptotic effect. The administration may be simultaneous or separated in time; however, the agent which suppresses the glucose anaerobic pathway will be provided at a time and in an amount to suppress this pathway at the time the primary treatment is administered.

The treatment method of the invention is especially attractive as it offers a method to enhance the cytotoxic effect of antitumor compounds particularly in earlier stages of development of solid tumors where vascularization has not occurred to a significant extent.

EXAMPLE 1

Preparation of Formula 1

Apoptolidin was obtained by fermentation of Nocardiopsis sp. as described by Kim, J., et al. (supra) and treated with 0.2 M HCl in methanol for 3 hours at room temperature.

The reaction mixture was subjected to preparative reverse-phase HPLC with a full linear gradient from 100% water to 100% acetonitrile in 60 minutes at 15 ml/min on a Beckman C18 column (21.2 mm×15 cm).

The fraction containing the product of formula 1 was obtained in 12% yield. The structure of the product was confirmed by NMR and mass spectrometry. The disappearance of oleandrose and olivomycose was established by disappearance of peaks corresponding to these residues from COSY and HMQC spectra. The molecular formula was confirmed by FAB-MS to be $C_{44}H_{68}O_{13}$ [m/z 827.4667(M+Na)$^+$11.0 mmu] consistent with the compound of formula 1 less a molecule of water.

EXAMPLE 2

Activity of the Invention Compound

Activity was measured by FACS staining for annexin V and by MTT assay.

A. Mouse B Cell Lymphoma

The mouse B cell lymphoma cell line LYAS was incubated with apoptolidin in a compound of formula 1 for 6 hours. The treating compounds were removed and the cells were stained with annexin V-CY5PE for 15 minutes and washed 3 times. Cells were analyzed on the FACSAN and the percentage of annexin V+ cells was quantified. The $IC_{50}$ of the compound of formula 1 was 10 $\mu$M; the $IC_{50}$ of apoptolidin was 100 nM.

B. Breast Carcinoma

The breast carcinoma cell line MCF-7 was tested in 96-well plates in triplicate. Dilutions of apoptolidin or the compound of formula 1 were added to the wells for 120 hours. MTT was then added to the wells at a final concentration of 0.5 mg/ml. The supernatant was removed and the crystals dissolved in 40 mM HCl and isopropanol. The plates were scanned on a microplate reader at 595 nm. The $IC_{50}$ of the compound of formula 1 was 10 $\mu$M; the $IC_{50}$ of apoptolidin was 90 nM.

It is seen that while still exhibiting an antitumor effect, the effect is less than that of apoptolidin.

EXAMPLE 3

Stability of the Compound of Formula 1

Stability was monitored by an analytical reverse phase HBLC using a Beckman C18 column (4.6 mm×25 cm). Stability was analyzed in this manner at pH 4, 7 and 10, both for apoptolidin and the compound of formula 1. At pH 4, apoptolidin retained its structure for 24 hours; the compound of formula 1 for at least 28 hours when observation was terminated.

At pH 7, apoptolidin immediate equilibrated to an unknown compound and decomposed with a half-life of about 5 hours. The compound of formula 1 remained intact for at least 28 hours. At pH 10, apoptolidin decomposed almost immediately, and the compound of formula 1 was again intact after 28 hours.

Preparation A

Isolation of Yeast Mitochondria

Crude yeast mitochondria were isolated from a lactate grown *Saccharomyces cerevisiae* strain DBY7286 (mata, ura-/-) according to published procedures. Briefly, 2 L shake flasks of yeast were grown up on semisynthetic lactate medium at 30° C. with vigorous shaking to an OD600 of 3. Cells were collected at 4000 g and the wet weight of the pellet was determined. Cells were converted to spheroplasts by a 30 minute incubation at 30° C. with 2.5 mg Zymolyase 20T (ICN Biochemicals) per gram of packed cells in a volume of 2 ml per gram of packed cells in Buffer A (1.2 M sorbitol, 20 mM potassium phosphate, pH 7.4). The Zymolyase 20T was washed out twice by centrifugation at 4000 g and resuspension in Buffer A. The spheroplasts were then resuspended in Buffer B (0.6 M sorbitol, 20 mM $K^+$ MES, pH6.0) with 0.5 mM PMSF and homogenized in a 40 ml glass Dounce homogenizer using 15 strokes with a tight-fitting pestle. The unbroken spheroplasts were collected by centrifugation at 1500 g and rehomogenized with 15 strokes in Buffer B plus PMSF. The nuclei and unbroken cells were separated by centrifugation at 1500 g and the mitochondria were isolated from the supernatant by centrifugation at 12,000 g for 10 minutes. The mitochondrial pellet was then washed with Buffer B and collected at 12,000 g for 10 minutes. The protein concentration was determined by the Lowry assay and the dark brown mitochondria were resuspended in Buffer C (0.6 M sorbitol, 20 mM HEPES, pH 7.4). Mitochondria were prepared fresh and ATPase activity was measured within 6 hours.

EXAMPLE 4

Assay for Yeast Mitochondrial ATPase Activity

Mitochondrial ATPase activity was measured by standard methods. Briefly, 20 μg of yeast mitochondrial protein (as measured by the Lowry method) was added to reaction buffer containing 50 mM Tris (pH 8.0), 1 mM ATP, 0.3 mM NADH, 3.3 mM $MgCl_2$, 2 μg/ml antimycin A, 1 mM phosphoenol pyruvate, 5 U/ml lactate dehydrogenase, and 2.5 U/ml pyruvate kinase at 28° C. Oxidation of NADH was followed at 360 nm over time.

The results of a typical assay are shown in FIG. 9. As shown, in the absence of mitochondrial ATPase, no NADH is consumed over 15 minutes; similarly, without LDH or pyruvate kinase, no reaction occurs.

However, in the presence of 20 μg of yeast mitochondrial protein, with the reagents set forth above, NADH is depleted to 0 within 5 minutes. However, in the presence either of 80 μM oligomycin or 87 μM apoptolidin, the consumption of NADH is dramatically reduced.

What is claimed is:

1. A method to identify a compound which will effect apoptosis selectively in tumors, which method comprises assessing a candidate compound for its ability to inhibit mitochondrial ATP synthase, whereby a compound which is able to inhibit said synthase is identified as a compound that will selectively effect apoptosis in tumors;

wherein said candidate compound is an analog of apoptolidin.

2. The method of claim 1 wherein said assessing is by assessing the ATPase activity of said synthase.

3. The method of claim 2 wherein said ATP synthase is obtained from yeast.

4. The method of claim 1 wherein said analog is produced from a modified form of the synthase for apoptolidin or of its tailoring enzymes.

* * * * *